United States Patent [19]
Sreekrishna et al.

[11] Patent Number: 6,060,299
[45] Date of Patent: May 9, 2000

[54] ENZYME EXHIBITING MANNASE ACTIVITY, CLEANING COMPOSITIONS, AND METHODS OF USE

[75] Inventors: Kotikanyadanam Sreekrishna; Kevin Johnstone, both of Cincinnati; Charles Saunders, Fairfield, all of Ohio; Jean-Luc Bettiol, Brussels, Belgium

[73] Assignee: Novo Nordisk A/S, Bagsvaerd, Denmark

[21] Appl. No.: 09/095,163

[22] Filed: Jun. 10, 1998

[51] Int. Cl.[7] ............................. C12N 9/24; D06M 16/00
[52] U.S. Cl. ......................... 435/200; 435/263; 435/264; 510/300; 510/305; 510/530
[58] Field of Search ...................... 435/200, 263, 435/264; 510/300, 305, 530

[56] References Cited

FOREIGN PATENT DOCUMENTS

| | | |
|---|---|---|
| WO 91/18974 | 12/1991 | WIPO . |
| WO 93/24622 | 12/1993 | WIPO . |
| WO 94/25576 | 11/1994 | WIPO . |
| WO 95/35362 | 12/1995 | WIPO . |
| WO 97/11164 | 3/1997 | WIPO . |

OTHER PUBLICATIONS

Kunst et al. (1997) The complete genome sequence of the Gram–positive bacterium *Bacillus subtilis*. Nature 390: 249–256.
Talbot et al., Appl. Environ. Microbiol vol. 56, No. 11, pp. 3505–3510 (1990).
Mendoza et al., World J. Microbiol Biotech., vol. 10, No. 5, pp. 551–555, (1994).
Abstract of JP–0304706, (1991).
Abstract of JP–63056289, (1988).
Abstract of JP–63036774, (1988).
Abstract of JP—08051975, (1996).

*Primary Examiner*—Lisa J. Hobbs
*Attorney, Agent, or Firm*—Steve T. Zelson, Esq.; Elias J. Lambiris, Esq.

[57] ABSTRACT

Novel mannanases may be derived from eg *Bacillus subtilis* strain 168 or may be encoded by polynucleotide molecules comprising a nucleotide sequence as shown in SEQ ID NO: 1. The mannanases are alkaline and are useful e.g. in cleaning compositions, for modifying plant material, and for treatment of cellulosic fibres.

19 Claims, No Drawings

ENZYME EXHIBITING MANNASE ACTIVITY, CLEANING COMPOSITIONS, AND METHODS OF USE

The present invention relates to microbial mannanases, more specifically to microbial enzymes exhibiting mannanase activity as their major enzymatic activity in the neutral and alkaline pH ranges; to a method of producing such enzymes; and to methods for using such enzymes in the paper and pulp, textile, cleaning and cellulose fiber processing industries.

BACKGROUND OF THE INVENTION

Mannan containing polysaccharides are a major component of the hemicellulose fraction in woods and endosperm in many leguminous seeds and in some mature seeds of non-leguminous plants. Essentially unsubstituted linear beta-1,4-mannan is found in some non-leguminous plants. Unsubstituted beta-1,4-mannan which is present e.g. in ivory nuts resembles cellulose in the conformation of the individual polysaccharide chains, and is water-insoluble. In leguminous seeds, water-soluble galactomannan is the main storage carbohydrate comprising up to 20% of the total dry weight. Galactomannans have a linear beta-1,4-mannan backbone substituted with single alpha-1,6-galactose, optionally substituted with acetyl groups. Mannans are also found in several monocotyledonous plants and are the most abundant polysaccharides in the cell wall material in palm kernel meal. Glucomannans are linear polysaccharides with a backbone of beta-1,4-linked mannose and glucose alternating in a more or less regular manner, the backbone optionally being substituted with galactose and/or acetyl groups. Mannans, galactomannans, glucomannans and galactoglucomannans (i.e. glucomannan backbones with branched galactose) contribute to more than 50% of the softwood hemicellulose. Moreover, the cellulose of many red algae contains a significant amount of mannose.

Mannanases have been identified in several Bacillus organisms. For example, Talbot et al., Appl. Environ. Microbiol., Vol.56, No. 11, pp. 3505–3510 (1990) describes a beta-mannanase derived from *Bacillus stearothermophilus* in dimer form having molecular weight of 162 kDa and an optimum pH of 5.5–7.5. Mendoza et al., World J. Microbiol. Biotech., Vol. 10, No. 5, pp. 551–555 (1994) describes a beta-mannanase derived from *Bacillus subtilis* having a molecular weight of 38 kDa, an optimum activity at pH 5.0 and 55° C. and a pI of 4.8. JP-0304706 discloses a beta-mannanase derived from Bacillus sp., having a molecular weight of 37±3 kDa measured by gel filtration, an optimum pH of 8–10 and a pI of 5.3–5.4. JP-63056289 describes the production of an alkaline, thermostable beta-mannanase which hydrolyses beta-1,4-D-mannopyranoside bonds of e.g. mannans and produces manno-oligosaccharides. JP-63036774 relates to the Bacillus microorganism FERM P-8856 which produces beta-mannanse and beta-mannosidase at an alkaline pH. JP-08051975 discloses alkaline beta-mannanases from alkalophilic Bacillus sp. AM-001. A purified mannanase from Bacillus amyloliquefaciens useful in the bleaching of pulp and paper and a method of preparation thereof is disclosed in WO 97/11164. WO 91/18974 describes a hemicellulase such as a glucanase, xylanase or mannanase active at an extreme pH and temperature. WO 94/25576 discloses an enzyme from Aspergillus aculeatus, CBS 101.43, exhibiting mannanase activity which may be useful for degradation or modification of plant or algae cell wall material. WO 93/24622 discloses a mannanase isolated from *Trichoderma reseei* useful for bleaching lignocellulosic pulps.

WO 95/35362 discloses cleaning compositions containing plant cell wall degrading enzymes having pectinase and/or hemicellulase and optionally cellulase activity for the removal of stains of vegetable origin and further discloses an alkaline mannanase from the strain C11SB.G17.

It is an object of the present invention to provide a novel and efficient enzyme exhibiting mannanase activity also in the alkaline pH range, e.g. when applied in cleaning compositions or different industrial processes.

SUMMARY OF THE INVENTION

The inventors have now found a novel enzyme having substantial mannanase activity, i.e. an enzyme exhibiting mannanase activity which may be obtained from a bacterial strain of the genus Bacillus, more specifically of the strain *Bacillus subtilis*, by identifying a DNA sequence encoding such enzyme. The DNA sequence and the deduced amino acid sequence are listed in the sequence listing as SEQ ID No. 1 and 2, respectively. It is believed that the novel enzyme will be classified according to the Enzyme Nomenclature in the Enzyme Class EC 3.2.1.78.

In a first aspect, the present invention relates to a mannanase which is i) a polypeptide produced by *Bacillus subtilis* strain 168, or ii) a polypeptide comprising an amino acid sequence as shown in SEQ ID NO:2, or iii) an analogue of the polypeptide defined in i) or ii) which is at least 80% homologous with said polypeptide, is derived from said polypeptide by substitution, deletion or addition of one or several amino acids, or is immunologically reactive with a polyclonal antibody raised against said polypeptide in purified form.

Within one aspect, the present invention provides an isolated polynucleotide molecule selected from the group consisting of (a) polynucleotide molecules encoding a polypeptide having mannanase activity and comprising a sequence of nucleotides as shown in SEQ ID NO: 1; (b) species homologs of (a); (c) polynucleotide molecules that encode a polypeptide having mannanase activity that is at least 80% identical to the amino acid sequence of SEQ ID NO: 2; (d) molecules complementary to (a), (b) or (c); and (e) degenerate nucleotide sequences of (a), (b), (c) or (d).

Within another aspect of the invention there is provided an expression vector comprising the following operably linked elements: a transcription promoter; a DNA segment selected from the group consisting of (a) polynucleotide molecules encoding a polypeptide having mannanase activity and comprising a sequence of nucleotides as shown in SEQ ID NO: 1; (b) species homologs of (a); (c) polynucleotide molecules that encode a polypeptide having mannanase activity that is at least 80% identical to the amino acid sequence of SEQ ID NO: 2; and (d) degenerate nucleotide sequences of (a), (b), or (c); and a transcription terminator.

Within yet another aspect of the present invention there is provided a cultured cell into which has been introduced an expression vector as disclosed above, wherein said cell expresses the polypeptide encoded by the DNA segment.

A further aspect of the present invention provides an isolated polypeptide having mannanase activity selected from the group consisting of (a) polypeptide molecules comprising a sequence of amino acid residues as shown in SEQ ID NO:2; (b) species homologs of (a).

Within another aspect of the present invention there is provided a composition comprising a purified polypeptide according to the invention in combination with other polypeptides.

Within another aspect of the present invention there are provided methods for producing a polypeptide according to the invention comprising culturing a cell into which has been introduced an expression vector as disclosed above, whereby said cell expresses a polypeptide encoded by the DNA segment and recovering the polypeptide.

The novel enzyme of the present invention is useful for the treatment of cellulosic material, especially cellulose-containing fiber, yarn, woven or non-woven fabric, treatment of mechanical paper-making pulps, kraft pulps or recycled waste paper, and for retting of fibres. The treatment can be carried out during the processing of cellulosic material into a material ready for manufacture of paper or of garment or fabric, the latter e.g. in the desizing or scouring step; or during industrial or household laundering of such fabric or garment.

Accordingly, in further aspects the present invention relates to a cleaning or detergent composition comprising an enzyme having substantial mannanase activity; and to use of the enzyme of the invention for the treatment, eg cleaning, of cellulose-containing fibers, yarn, woven or non-woven fabric, as well as synthetic or partly synthetic fabric.

The enzyme of the invention is very effective for use in an enzymatic scouring process and/or desizing (removal of mannan size) in the preparation of cellulosic material e.g. for proper response in subsequent dyeing operations. The enzyme is also useful for removal of mannan containing print paste. Further, detergent compositions comprising the novel enzyme are capable of removing or bleaching certain soils or stains present on laundry, especially soils and spots resulting from mannan containing food, plants, and the like. Further, treatment with leaning or detergent compositions comprising the novel enzyme an prevent binding of certain soils to the cellulosic material.

Accordingly, the present invention also relates to cleaning compositions, including laundry, dishwashing, hard surface cleaner, personal cleansing and oral/dental compositions, comprising a mannanase and a bioscouring enzyme selected from cellulases, amylases, pectin degrading enzymes, and/or xyloglucanases, such compositions providing superior cleaning performance, i.e. superior stain removal, dingy cleaning and whiteness maintenance.

DEFINITIONS

Prior to discussing this invention in further detail, the following terms will first be defined.

The term "ortholog" (or "species homolog") denotes a polypeptide or protein obtained from one species that has homology to an analogous polypeptide or protein from a different species.

The term "paralog" denotes a polypeptide or protein obtained from a given species that has homology to a distinct polypeptide or protein from that same species.

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. The expression vector of the invention may be any expression vector that is conveniently subjected to recombinant DNA procedures, and the choice of vector will often depend on the host cell into which the vector is to be introduced. Thus, the vector may be an autonomously replicating vector, i.e. a vector which exists as an extra-chromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The term "recombinant expressed" or "recombinantly expressed" used herein in connection with expression of a polypeptide or protein is defined according to the standard definition in the art. Recombinantly expression of a protein is generally performed by using an expression vector as described immediately above.

The term "isolated", when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985). The term "an isolated polynucleotide" may alternatively be termed "a cloned polynucleotide".

When applied to a protein/polypeptide, the term "isolated" indicates that the protein is found in a condition other than its native environment. In a preferred form, the isolated protein is substantially free of other proteins, particularly other homologous proteins (i.e. "homologous impurities" (see below)). It is preferred to provide the protein in a greater than 40% pure form, more preferably greater than 60% pure form.

Even more preferably it is preferred to provide the protein in a highly purified form, i.e., greater than 80% pure, more preferably greater than 95% pure, and even more preferably greater than 99% pure, as determined by SDS-PAGE.

The term "isolated protein/polypeptide" may alternatively be termed "purified protein/polypeptide".

The term "homologous impurities" means any impurity (e.g. another polypeptide than the polypeptide of the invention) which originate from the homologous cell where the polypeptide of the invention is originally obtained from.

The term "obtained from" as used herein in connection with a specific microbial source, means that the polynucleotide and/or polypeptide produced by the specific source, or by a cell in which a gene from the source have been inserted.

The term "operably linked", when referring to DNA segments, denotes that the segments are arranged so that they function in concert for their intended purposes, e.g. transcription initiates in the promoter and proceeds through the coding segment to the terminator The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "complements of polynucleotide molecules" denotes polynucleotide molecules having a complementary base sequence and reverse orientation as compared to a reference sequence. For example, the sequence 5' ATG-CACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "promoter" denotes a portion of a gene containing DNA sequences that provide for the binding of RNA polymerase and initiation of transcription. Promoter sequences are commonly, but not always, found in the 5' non-coding regions of genes.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

The term "mannanase" or "galactomannanase" denotes a mannanase enzyme defined according to the art as officially being named mannan endo-1,4-beta-mannosidase and having the alternative names beta-mannanase and endo-1,4-mannanase and catalysing the reaction: random hydrolyses of 1,4-beta-D-mannosidic linkages in mannans, galactomannans, glucomannans, and galactoglucomannans.

DETAILED DESCRIPTION OF THE INVENTION

HOW TO USE A SEQUENCE OF THE INVENTION TO GET OTHER RELATED SEQUENCES

The disclosed sequence information herein relating to a polynucleotide sequence encoding a mannanase of the invention can be used as a tool to identify other homologous mannanases. For instance, polymerase chain reaction (PCR) can be used to amplify sequences encoding other homologous mannanases from a variety of microbial sources, in particular of different Bacillus species.

ASSAY FOR ACTIVITY TEST

A polypeptide of the invention having mannanase activity may be tested for mannanase activity according to standard test procedures known in the art, such as by applying a solution to be tested to 4 mm diameter holes punched out in agar plates containing 0.2% AZCL galactomannan (carob), i.e. substrate for the assay of endo-1,4-beta-D-mannanase available as CatNo.I-AZGMA from the company Megazyme (Megazyme's Internet address: http://www.megazyme.com/Purchase/index.html).

POLYNUCLEOTIDES

Within preferred embodiments of the invention an isolated polynucleotide of the invention will hybridize to similar sized regions of SEQ ID No. 1, or a sequence complementary thereto, under at least medium stringency conditions.

In particular polynucleotides of the invention will hybridize to a denatured double-stranded DNA probe comprising either the full sequence shown in SEQ ID NO: 1 or any probe comprising a subsequence of SEQ ID NO: 1 having a length of at least about 100 base pairs under at least medium stringency conditions, but preferably at high stringency conditions as described in detail below. Suitable experimental conditions for determining hybridization at medium, or high stringency between a nucleotide probe and a homologous DNA or RNA sequence involves presoaking of the filter containing the DNA fragments or RNA to hybridize in 5×SSC (Sodium chloride/Sodium citrate, Sambrook et al. 1989) for 10 min, and prehybridization of the filter in a solution of 5×SSC, 5×Denhardt's solution (Sambrook et al. 1989), 0.5% SDS and 100 µg/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) Anal. Biochem. 132:6–13), 32P-dCTP-labeled (specific activity higher than 1×109 cpm/µg) probe for 12 hours at ca. 45° C. The filter is then washed twice for 30 minutes in 2×SSC, 0.5% SDS at least 60° C. (medium stringency), still more preferably at least 65° C. (medium/high stringency), even more preferably at least 70° C. (high stringency), and even more preferably at least 75° C. (very high stringency).

Molecules to which the oligonucleotide probe hybridizes under these conditions are detected using a x-ray film.

As previously noted, the isolated polynucleotides of the present invention include DNA and RNA. Methods for isolating DNA and RNA are well known in the art. DNA and RNA encoding genes of interest can be cloned in Gene Banks or DNA libraries by means of methods known in the art.

Polynucleotides encoding polypeptides having mannanase activity of the invention are then identified and isolated by, for example, hybridization or PCR.

The present invention further provides counterpart polypeptides and polynucleotides from different bacterial strains (orthologs or paralogs). Of particular interest are mannanase polypeptides from gram-positive alkalophilic strains, including species of Bacillus.

Species homologues of a polypeptide with mannanase activity of the invention can be cloned using information and compositions provided by the present invention in combination with conventional cloning techniques. For example, a DNA sequence of the present invention can be cloned using chromosomal DNA obtained from a cell type that expresses the protein. Suitable sources of DNA can be identified by probing Northern blots with probes designed from the sequences disclosed herein. A library is then prepared from chromosomal DNA of a positive cell line. A DNA sequence of the invention encoding an polypeptide having mannanase activity can then be isolated by a variety of methods, such as by probing with probes designed from the sequences disclosed in the present specification and claims or with one or more sets of degenerate probes based on the disclosed sequences. A DNA sequence of the invention can also be cloned using the polymerase chain reaction, or PCR (Mullis, U.S. Pat. No. 4,683,202), using primers designed from the sequences disclosed herein. Within an additional method, the DNA library can be used to transform or transfect host cells, and expression of the DNA of interest can be detected with an antibody (monoclonal or polyclonal) raised against the mannanase cloned from B. subtilis strain 168 and purified as described in Example 1, or by an activity test relating to a polypeptide having mannanase activity.

The mannanase encoding part of the DNA sequence and/or an analogue DNA sequence of the invention may be cloned from a strain of the bacterial species Bacillus subtilis, preferably the strain 168, producing the enzyme with mannan degrading activity, or another or related organism as described herein.

Alternatively, the analogous sequence may be constructed on the basis of the DNA sequence e.g be a sub-sequence thereof eg by introduction of nucleotide substitutions which do not give rise to another amino acid sequence of the mannanase encoded by the DNA sequence, but which corresponds to the codon usage of the host organism intended for production of the enzyme, or by introduction of nucleotide substitutions which may give rise to a different amino acid sequence (i.e. a variant of the mannan degrading enzyme of the invention).

POLYPEPTIDES

The sequence of amino acids of SEQ ID NO: 2 is a mature mannanase sequence.

The present invention also provides mannanase polypeptides that are substantially homologous to the polypeptide of SEQ ID NO:2 and species homologs (paralogs or orthologs) thereof. The term "substantially homologous" is used herein to denote polypeptides having 70%, preferably at least 80%, more preferably at least 85%, and even more preferably at least 90%, sequence identity to the sequence shown in SEQ ID NO:2 or their orthologs or paralogs. Such polypeptides will more preferably be at least 95% identical, and most preferably 98% or more identical to the sequence shown in SEQ ID NO:2 or its orthologs or paralogs. Percent sequence identity is determined by conventional methods, by means of computer programs known in the art such as GAP provided in the GCG program package (Program Manual for the Wisconsin Package, Version 8, August 1994, Genetics Computer Group, 575 Science Drive, Madison, Wis., U.S.A. 53711) as disclosed in Needleman, S. B. and Wunsch, C. D., (1970), Journal of Molecular Biology, 48, 443–453, which is hereby incorporated by reference in its entirety. GAP is used with the following settings for polypeptide sequence comparison: GAP creation penalty of 3.0 and GAP extension penalty of 0.1.

Sequence identity of polynucleotide molecules is determined by similar methods using GAP with the following settings for DNA sequence comparison: GAP creation penalty of 5.0 and GAP extension penalty of 0.3.

The enzyme preparation of the invention is preferably derived from a microorganism, preferably from a bacterium, an archea or a fungus, especially from a bacterium such as a bacterium belonging to Bacillus, preferably to an alkalophilic Bacillus strain which may be selected from the group consisting of the species *Bacillus subtilis* and highly related Bacillus species in which all species preferably are at least 95%, even more preferably at least 98%, homologous to *Bacillus subtilis* based on aligned 16S rDNA sequences.

Substantially homologous proteins and polypeptides are characterized as having one or more amino acid substitutions, deletions or additions. These changes are preferably of a minor nature, that is conservative amino acid substitutions (see Table 2) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a poly-histidine tract, protein A (Nilsson et al., *EMBO J.* 4:1075, 1985; Nilsson et al., *Methods Enzymol.* 198:3, 1991. See, in general Ford et al., *Protein Expression and Purification* 2: 95–107, 1991, which is incorporated herein by reference. DNAs encoding affinity tags are available from commercial suppliers (e.g., Pharmacia Biotech, Piscataway, N.J.; New England Biolabs, Beverly, Mass.).

However, even though the changes described above preferably are of a minor nature, such changes may also be of a larger nature such as fusion of larger polypeptides of up to 300 amino acids or more both as amino- or carboxyl-terminal extensions to a Mannanase polypeptide of the invention.

TABLE 1

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

In addition to the 20 standard amino acids, non-standard amino acids (such as 4-hydroxyproline, 6-N-methyl lysine, 2-aminoisobutyric acid, isovaline and a-methyl serine) may be substituted for amino acid residues of a polypeptide according to the invention. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, or preferably, are commercially available, and include pipecolic acid, thiazolidine carboxylic acid, dehydroproline, 3- and 4-methylproline, and 3,3-dimethylproline.

Essential amino acids in the mannanase polypeptides of the present invention can be identified according to procedures known in the art, such as site-directed mutagenesis or alanine-scanning mutagenesis (Cunningham and Wells, *Science* 244: 1081–1085, 1989). In the latter technique, single alanine mutations are introduced at every residue in the molecule, and the resultant mutant molecules are tested for biological activity (i.e mannanase activity) to identify amino acid residues that are critical to the activity of the molecule. See also, Hilton et al., *J. Biol. Chem.* 271:4699–4708, 1996. The active site of the enzyme or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–312, 1992; Smith et al., *J. Mol. Biol.* 224:899–904, 1992; Wlodaver et al., *FEBS Lett.* 309:59–64, 1992. The identities of essential amino acids can also be inferred from analysis of homologies with polypeptides which are related to a polypeptide according to the invention.

Multiple amino acid substitutions can be made and tested using known methods of mutagenesis, recombination and/or shuffling followed by a relevant screening procedure, such as those disclosed by Reidhaar-Olson and Sauer (*Science*

241:53–57, 1988), Bowie and Sauer (*Proc. Natl. Acad. Sci. USA* 86:2152–2156, 1989), WO95/17413, or WO 95/22625. Briefly, these authors disclose methods for simultaneously randomizing two or more positions in a polypeptide, or recombination/shuffling of different mutations (WO95/17413, WO95/22625), followed by selecting for functional a polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Mutagenesis/shuffling methods as disclosed above can be combined with high-throughput, automated screening methods to detect activity of cloned, mutagenized polypeptides in host cells. Mutagenized DNA molecules that encode active polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are substantially homologous to residues 32 to 343 of SEQ ID NO: 2 and retain the mannanase activity of the wild-type protein.

The mannanase enzyme of the invention may, in addition to the enzyme core comprising the catalytically domain, also comprise a cellulose binding domain (CBD), the cellulose binding domain and enzyme core (the catalytically active domain) of the enzyme being operably linked. The cellulose binding domain (CBD) may exist as an integral part of the encoded enzyme, or a CBD from another origin may be introduced into the mannan degrading enzyme thus creating an enzyme hybrid. In this context, the term "cellulose-binding domain" is intended to be understood as defined by Peter Tomme et al. "Cellulose-Binding Domains: Classification and Properties" in "Enzymatic Degradation of Insoluble Carbohydrates", John N. Saddler and Michael H. Penner (Eds.), ACS Symposium Series, No. 618, 1996. This definition classifies more than 120 cellulose-binding domains into 10 families (I-X), and demonstrates that CBDs are found in various enzymes such as cellulases, xylanases, mannanases, arabinofuranosidases, acetyl esterases and chitinases. CBDs have also been found in algae, e.g. the red alga *Porphyra purpurea* as a non-hydrolytic polysaccharide-binding protein, see Tomme et al., op.cit. However, most of the CBDs are from cellulases and xylanases, CBDs are found at the N and C termini of proteins or are internal. Enzyme hybrids are known in the art, see e.g. WO 90/00609 and WO 95/16782, and may be prepared by transforming into a host cell a DNA construct comprising at least a fragment of DNA encoding the cellulose-binding domain ligated, with or without a linker, to a DNA sequence encoding the mannan degrading enzyme and growing the host cell to express the fused gene. Enzyme hybrids may be described by the following formula:

CBD—MR—X wherein CBD is the N-terminal or the C-terminal region of an amino acid sequence corresponding to at least the cellulose-binding domain; MR is the middle region (the linker), and may be a bond, or a short linking group preferably of from about 2 to about 100 carbon atoms, more preferably of from 2 to 40 carbon atoms; or is preferably from about 2 to to about 100 amino acids, more preferably of from 2 to 40 amino acids; and X is an N-terminal or C-terminal region of the mannanase of the invention.

Preferably, the mannanase enzyme of the present invention has its maximum catalytic activity at a pH of at least 8, more preferably of at least 8.5, more preferably of at least 9, more preferably of at least 9.5, more preferably of at least 10, even more preferably of at least 10.5, especially of at least 11; and preferably the maximum activity of the enzyme is obtained at a temperature of at least 50° C., more preferably of at least 55° C.

PROTEIN PRODUCTION

The proteins and polypeptides of the present invention, including full-length proteins, fragments thereof and fusion proteins, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Bacterial cells, particularly cultured cells of gram-positive organisms, are preferred. Gram-positive cells from the genus of Bacillus are especially preferred, such as from the group consisting of *Bacillus subtilis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus thuringiensis, Bacillus licheniformis,* and *Bacillus agaradherens,* in particular *Bacillus subtilis.*

Techniques for manipulating cloned DNA molecules and introducing exogenous DNA into a variety of host cells are disclosed by Sambrook et al., *Molecular Cloning: A Laboratory Manual,* 2nd ed., Cold Spring Harbor Laboratory Press, Cold Spring Harbor, N.Y., 1989; Ausubel et al. (eds.), *Current Protocols in Molecular Biology,* John Wiley and Sons, Inc., NY, 1987; and *"Bacillus subtilis* and Other Gram-Positive Bacteria", Sonensheim et al., 1993, American Society for Microbiology, Washington D.C., which are incorporated herein by reference.

In general, a DNA sequence encoding a mannanase of the present invention is operably linked to other genetic elements required for its expression, generally including a transcription promoter and terminator within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a polypeptide into the secretory pathway of a host cell, a secretory signal sequence (also known as a leader sequence, prepro sequence or pre sequence) is provided in the expression vector. The secretory signal sequence may be that of the polypeptide, or may be derived from another secreted protein or synthesized de novo. Numerous suitable secretory signal sequences are known in the art and reference is made to *"Bacillus subtilis* and Other Gram-Positive Bacteria", Sonensheim et al., 1993, American Society for Microbiology, Washington D.C.; and Cutting, S. M.(eds.)

"Molecular Biological Methods for Bacillus", John Wiley and Sons, 1990, for further description of suitable secretory signal sequences especially for secretion in a Bacillus host cell. The secretory signal sequence is joined to the DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

PROTEIN ISOLATION

When the expressed recombinant polypeptide is secreted the polypeptide may be purified from the growth media. Preferably the expression host cells are removed from the media before purification of the polypeptide (e.g. by centrifugation).

When the expressed recombinant polypeptide is not secreted from the host cell, the host cell are preferably disrupted and the polypeptide released into an aqueous "extract" which is the first stage of such purification techniques. Preferably the expression host cells are collected from the media before the cell disruption (e.g. by centrifugation).

The cell disruption may be performed by conventional techniques such as by lysozyme digestion or by forcing the cells through high pressure. See (Robert K. Scobes, Protein Purification, Second edition, Springer-Verlag) for further description of such cell disruption techniques.

Whether or not the expressed recombinant polypeptides (or chimeric polypeptides) is secreted or not it can be purified using fractionation and/or conventional purification methods and media.

Ammonium sulfate precipitation and acid or chaotrope extraction may be used for fractionation of samples. Exemplary purification steps may include hydroxyapatite, size exclusion, FPLC and reverse-phase high performance liquid chromatography. Suitable anion exchange media include derivatized dextrans, agarose, cellulose, polyacrylamide, specialty silicas, and the like. PEI, DEAE, QAE and Q derivatives are preferred, with DEAE Fast-Flow Sepharose (Pharmacia, Piscataway, N.J.) being particularly preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers.

Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

Polypeptides of the invention or fragments thereof may also be prepared through chemical synthesis. Polypeptides of the invention may be monomers or multimers; glycosylated or non-glycosylated; pegylated or non-pegylated; and may or may not include an initial methionine amino acid residue.

Based on the sequence information disclosed herein a full length DNA sequence encoding a mannanase of the invention and comprising the DNA sequence shown in SEQ ID No 1 may be cloned.

Cloning is performed by standard procedures known in the art such as by, preparing a genomic library from a Bacillus strain, especially the strain *B. subtilis* 168;

plating such a library on suitable substrate plates;

identifying a clone comprising a polynucleotide sequence of the invention by standard hybridization techniques using a probe based on SEQ ID No 1; or by identifying a clone from said *Bacillus subtilis* 168 genomic library by an Inverse PCR strategy using primers based on sequence information from SEQ ID No 1. Reference is made to M. J. MCPherson et al. ("PCR A practical approach" Information Press Ltd, Oxford England) for further details relating to Inverse PCR.

Based on the sequence information disclosed herein (SEQ ID No 1, SEQ ID No 2) is it routine work for a person skilled in the art to isolate homologous polynucleotide sequences encoding homologous mannanase of the invention by a similar strategy using genomic libraries from related microbial organisms, in particular from genomic libraries from other strains of the genus Bacillus such as alkalophilic species of Bacillus.

In the present context, the term "enzyme preparation" is intended to mean either a conventional enzymatic fermentation product, possibly isolated and purified, from a single species of a microorganism, such preparation usually comprising a number of different enzymatic activities; or a mixture of monocomponent enzymes, preferably enzymes derived from bacterial or fungal species by using conventional recombinant techniques, which enzymes have been fermented and possibly isolated and purified separately and which may originate from different species, preferably fungal or bacterial species; or the fermentation product of a microorganism which acts as a host cell for expression of a recombinant mannanase, but which microorganism simultaneously produces other enzymes, e.g. pectin degrading enzymes, proteases, or cellulases, being naturally occurring fermentation products of the microorganism, i.e. the enzyme complex conventionally produced by the corresponding naturally occurring microorganism.

The mannanase preparation of the invention may further comprise one or more enzymes selected from the group consisting of proteases, cellulases (endo-$\beta$-1,4-glucanases), β-glucanases (endo-β-1,3(4)-glucanases), lipases, cutinases, peroxidases, laccases, amylases, glucoamylases, pectinases, reductases, oxidases, phenoloxidases, ligninases, pullulanases, hemicellulases, pectate lyases, xyloglucanases, xylanases, pectin acetyl esterases, rhamnogalacturonan acetyl esterases, polygalacturonases, rhamnogalacturonases, pectin lyases, pectin methylesterases, cellobiohydrolases, transglutaminases; or mixtures thereof. In a preferred embodiment, one or more or all enzymes in the preparation is produced by using recombinant techniques, i.e. the enzyme(s) is/are monocomponent enzyme(s) which is/are mixed with the other enzyme(s) to form an enzyme preparation with the desired enzyme blend.

In another aspect, the present invention also relates to a method of producing the enzyme preparation of the invention, the method comprising culturing a microorganism, eg a wild-type strain, capable of producing the mannanase under conditions permitting the production of the enzyme, and recovering the enzyme from the culture. Culturing may be carried out using conventional fermentation techniques e.g. culturing in shake flasks or fermentors with agitation to ensure sufficient aeration on a growth medium inducing production of the mannanase enzyme. The growth medium may contain a conventional N-source such as peptone, yeast extract or casamino acids, a reduced amount of a conventional C-source such as dextrose or sucrose, and an inducer such as guar gum or locust bean gum. The recovery may be carried out using conventional techniques, e.g. separation of bio-mass and supernatant by centrifugation or filtration, recovery of the supernatant or disruption of cells if the enzyme of interest is intracellular, perhaps followed by further purification as described in EP 0 406 314 or by crystallization as described in WO 97/15660.

IMMUNOLOGICAL CROSS-REACTIVITY

Polyclonal antibodies to be used in determining immunological cross-reactivity may be prepared by use of a purified mannanase enzyme. More specifically, antiserum against the mannanase of the invention may be raised by immunizing rabbits (or other rodents) according to the procedure described by N. Axelsen et al. in: A Manual of Quantitative Immunoelectrophoresis, Blackwell Scientific Publications, 1973, Chapter 23, or A. Johnstone and R. Thorpe, Immunochemistry in Practice, Blackwell Scientific Publications, 1982 (more specifically p. 27–31). Purified immunoglobulins may be obtained from the antisera, for example by salt precipitation (($NH_4$)$_2$ $SO_4$), followed by dialysis and ion exchange chromatography, e.g. on DEAE-Sephadex. Immunochemical characterization of proteins may be done either by Outcherlony double-diffusion analysis (O. Ouchterlony in: Handbook of Experimental Immunology (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2).

Examples of useful bacteria producing the enzyme or the enzyme preparation of the invention are Gram positive bacteria, preferably from the Bacillus/Lactobacillus subdivision, preferably a strain from the genus Bacillus, more preferably a strain of *Bacillus subtilis,* esepcially the strain *Bacillus subtilis* 168.

In yet another aspect, the present invention relates to an isolated mannanase having the properties described above and which is free from homologous impurities, and is produced using conventional recombinant techniques.

Use in the detergent industry

In further aspects, the present invention relates to a detergent composition comprising the mannanase or mannanase preparation of the invention, to a process for machine treatment of fabrics comprising treating fabric during a washing cycle of a machine washing process with a washing solution containing the mannanase or mannanase preparation of the invention, and to cleaning compositions, including laundry, dishwashing, hard surface cleaner, personal cleansing and oral/dental compositions, comprising a mannanase and a bioscouring enzyme selected from cellulases, amylases, pectin degrading enzymes, and/or xyloglucanases and providing superior cleaning performance, i.e. superior stain removal, dingy cleaning and whiteness maintenance.

Without being bound to this theory, it is believed that the mannanase of the present invention is capable of effectively degrading or hydrolysing any soiling or spots containing galatomannans and, accordingly, of cleaning laundry comprising such soilings or spots.

The cleaning compositions of the invention must contain at least one additional detergent component. The precise nature of these additional components, and levels of incorporation thereof will depend on the physical form of the composition, and the nature of the cleaning operation for which it is to be used.

The cleaning compositions of the present invention preferably further comprise a detergent ingredient selected from a selected surfactant, another enzyme, a builder and/or a bleach system.

The cleaning compositions according to the invention can be liquid, paste, gels, bars, tablets, spray, foam, powder or granular. Granular compositions can also be in "compact" form and the liquid compositions can also be in a "concentrated" form.

The compositions of the invention may for example, be formulated as hand and machine dishwashing compositions, hand and machine laundry detergent compositions including laundry additive compositions and compositions suitable for use in the soaking and/or pretreatment of stained fabrics, rinse added fabric softener compositions, and compositions for use in general household hard surface cleaning operations. Compositions containing such carbohydrases can also be formulated as sanitization products, contact lens cleansers and health and beauty care products such as oral/dental care and personal cleaning compositions.

When formulated as compositions for use in manual dishwashing methods the compositions of the invention preferably contain a surfactant and preferably other detergent compounds selected from organic polymeric compounds, suds enhancing agents, group II metal ions, solvents, hydrotropes and additional enzymes.

When formulated as compositions suitable for use in a laundry machine washing method, the compositions of the invention preferably contain both a surfactant and a builder compound and additionally one or more detergent components preferably selected from organic polymeric compounds, bleaching agents, additional enzymes, suds suppressors, dispersants, lime-soap dispersants, soil suspension and anti-redeposition agents and corrosion inhibitors. Laundry compositions can also contain softening agents, as additional detergent components. Such compositions containing carbohydrase can provide fabric cleaning, stain removal, whiteness maintenance, softening, colour appearance, dye transfer inhibition and sanitization when formulated as laundry detergent compositions.

The compositions of the invention can also be used as detergent additive products in solid or liquid form. Such additive products are intended to supplement or boost the performance of conventional detergent compositions and can be added at any stage of the cleaning process.

If needed the density of the laundry detergent compositions herein ranges from 400 to 1200 g/liter, preferably 500 to 950 g/liter of composition measured at 20° C.

The "compact" form of the compositions herein is best reflected by density and, in terms of composition, by the amount of inorganic filler salt; inorganic filler salts are conventional ingredients of detergent compositions in powder form; in conventional detergent compositions, the filler salts are present in substantial amounts, typically 17–35% by weight of the total composition. In the compact compositions, the filler salt is present in amounts not exceeding 15% of the total composition, preferably not exceeding 10%, most preferably not exceeding 5% by weight of the composition. The inorganic filler salts, such as meant in the present compositions are selected from the alkali and alkaline-earth-metal salts of sulphates and chlorides. A preferred filler salt is sodium sulphate.

Liquid detergent compositions according to the present invention can also be in a "concentrated form", in such case, the liquid detergent compositions according the present invention will contain a lower amount of water, compared to conventional liquid detergents. Typically the water content of the concentrated liquid detergent is preferably less than 40%, more preferably less than 30%, most preferably less than 20% by weight of the detergent composition.

Suitable specific detergent compounds for use herein are selected from the group consisting of the specific compounds as described in WO 97/01629 which is hereby incorporated by reference in its entirety.

Mannanase is incorporated into the cleaning compositions in accordance with the invention preferably at a level of from 0.0001% to 2%, more preferably from 0.0005% to 0.5%, most preferred from 0.001% to 0.1% pure enzyme by weight of the composition.

The cleaning compositions of the present invention further comprise as an essential element a bioscouring carbohydrase selected from cellulases, amylases, pectin degrading enzymes, and/or xyloglucanases. Preferably, the cleaning compositions of the present invention will comprise a mannanase, an amylase and abother bioscouring enzyme selected from cellulases, pectin degrading enzymes, and/or xyloglucanases.

The cellulases usable in the present invention include both bacterial or fungal cellulases. Preferably, they will have a pH optimum of between 5 and 12 and a specific activity above 50 CEVU/mg (Cellulose Viscosity Unit). Suitable cellulases are disclosed in U.S. Pat. No. 4,435,307, J61078384 and WO96/02653 which discloses fungal cellulase produced from *Humicola insolens*, Trichoderma, Thielavia and Sporotrichum, respectively. EP 739 982 describes cellulases isolated from novel Bacillus species. Suitable cellulases are also disclosed in GB-A-2075028; GB-A-2095275; DE-OS-22 47 832 and W095/26398.

Examples of such cellulases are cellulases produced by a strain of Humicola insolens (*Humicola grisea* var. *thermoidea*), particularly the strain *Humicola insolens*, DSM 1800. Other suitable cellulases are cellulases originated from *Humicola insolens* having a molecular weight of about 50 kD, an isoelectric point of 5.5 and containing 415 amino acids; and a ~43kD endo-beta-1,4-glucanase derived from Humicola insolens, DSM 1800; a preferred cellulase has the amino acid sequence disclosed in PCT Patent Application No. WO 91/17243. Also suitable cellulases are the EGIII cellulases from *Trichoderma longibrachiatum* described in W094/21801. Especially suitable cellulases are the cellulases having color care benefits. Examples of such cellulases are the cellulases described in WO 96/29397, EP-A-0495257, WO 91/17243, WO 91/17244 and WO 91/21801. Other suitable cellulases for fabric care and/or cleaning properties are described in W096/34092, WO 96/17994 and WO 95/24471.

Said cellulases are normally incorporated in the detergent composition at levels from 0.0001% to 2% of pure enzyme by weight of the detergent composition.

Preferred cellulases for the purpose of the present invention are alkaline cellulases, i.e. enzyme having at least 25%, more preferably at least 40% of their maximum activity at a pH ranging from 7 to 12. More preferred cellulases are enzymes having their maximum activity at a pH ranging from 7 to 12. A preferred alkaline cellulase is the cellulase sold under the tradename Carezyme® by Novo Nordisk A/S.

Amylases ($\alpha$ and/or $\beta$) can be included for removal of carbohydrate-based stains. WO 94/02597, Novo Nordisk A/S published Feb. 03, 1994, describes cleaning compositions which incorporate mutant amylases. See also WO 95/10603, Novo Nordisk A/S, published Apr. 20, 1995. Other amylases known for use in cleaning compositions include both $\alpha$- and $\beta$-amylases. $\alpha$-Amylases are known in the art and include those disclosed in U.S. Pat. No. 5,003,257; EP 252,666; WO/91/00353; FR 2,676,456; EP 285,123; EP 525,610; EP 368,341; and British Patent specification no. 1,296,839 (Novo). Other suitable amylases are stability-enhanced amylases described in WO 94/18314, published Aug. 18, 1994 and WO 96/05295, Genencor, published Feb. 22, 1996 and amylase variants having additional modification in the immediate parent available from Novo Nordisk A/S, disclosed in WO 95/10603, published April 95. Also suitable are amylases described in EP 277 216, W095/26397 and W096/23873 (all by Novo Nordisk).

Examples of commercial a-amylases products are Purafect Ox Am® from Genencor and Termamyl®, Ban®, Fungamyl® and Duramyl®, all available from Novo Nordisk A/S Denmark. W095/26397 describes other suitable amylases: $\alpha$-amylases characterised by having a specific activity at least 25% higher than the specific activity of Termamyl® at a temperature range of 25° C. to 55° C. and at a pH value in the range of 8 to 10, measured by the Phadebas ® $\alpha$-amylase activity assay. Suitable are variants of the above enzymes, described in W096/23873 (Novo Nordisk). Other amylolytic enzymes with improved properties with respect to the activity level and the combination of thermostability and a higher activity level are described in WO 95/35382.

Preferred amylases for the purpose of the present invention are the amylases sold under the tradename Termamyl, Duramyl and Maxamyl and or the a-amylase variant demonstrating increased thermostability disclosed as SEQ ID No. 2 in WO 96/23873.

Preferred amylases for specific applications are alkaline amylases, ie enzymes having an enzymatic activity of at least 10%, preferably at least 25%, more preferably at least 40% of their maximum activity at a pH ranging from 7 to 12. More preferred amylases are enzymes having their maximum activity at a pH ranging from 7 to 12.

The amylolytic enzymes are incorporated in the detergent compositions of the present invention a level of from 0.0001% to 2%, preferably from 0.00018% to 0.06%, more preferably from 0.00024% to 0.048% pure enzyme by weight of the composition.

The term "pectin degrading enzyme" is intended to encompass polygalacturonase (EC 3.2.1.15) exopolygalacturonase (EC 3.2.1.67), exo-poly-alpha-galacturonidase (EC 3.2.1.82), pectin lyase (EC 4.2.2.10), pectin esterase (EC 3.2.1.11), pectate lyase (EC 4.2.2.2), exo-polygalacturonate lyase (EC 4.2.2.9)and hemicellulases such as endo-1,3-β-xylosidase (EC 3.2.1.32), xylan-1,4-β-xylosidase (EC 3.2.1.37)and α-L-arabinofuranosidase (EC 3.2.1.55). The pectin degrading enzymes are natural mixtures of the above mentioned enzymatic activities. Pectin enzymes therefore include the pectin methylesterases which hydrolyse the pectin methyl ester linkages, polygalacturonases which cleave the glycosidic bonds between galacturonic acid molecules, and the pectin transeliminases or lyases which act on the pectic acids to bring about non-hydrolytic cleavage of α-1→4 glycosidic linkages to form unsaturated derivatives of galacturonic acid.

Pectin degrading enzymes are incorporated into the compositions in accordance with the invention preferably at a level of from 0.0001 % to 2 %, more preferably from 0.0005% to 0.5%, most preferred from 0.001 % to 0.1 % pure enzyme by weight of the total composition.

Preferred pectin degrading enzymes for specific applications are alkaline pectin degrading enzymes, ie enzymes having an enzymatic activity of at least 10%, preferably at least 25%, more preferably at least 40% of their maximum activity at a pH ranging from 7 to 12. More preferred pectin degrading enzymes are enzymes having their maximum activity at a pH ranging from 7 to 12. Alkaline pectin degrading enzymes are produced by alkalophilic microorganisms e.g. bacterial, fungal and yeast microorganisms such as Bacillus species. Preferred microorganisms are *Bacillus firmus, Bacillus circulans* and *Bacillus subtilis* as described in JP 56131376 and JP 56068393. Alkaline pectin decomposing enzymes include galacturan-1,4-α-galacturonase (EC 3.2.1.67), poly-galacturonase activities (EC 3.2.1.15, pectin esterase (EC 3.1.1.11), pectate lyase (EC 4.2.2.2) and their iso enzymes and they can be produced by the Erwinia species. Preferred are *E. chrysanthemi, E. carotovora, E. amylovora, E. herbicola, E. dissolvens* as described in JP 59066588, JP 63042988 and in *World J. Microbiol. Microbiotechnol.* (8, 2, 115–120) 1992. Said alkaline pectin enzymes can also be produced by Bacillus species as disclosed in JP 73006557 and Agr. Biol. Chem. (1972), 36(2) 285–93.

The term xyloglucanase encompasses the family of enzymes described by Vincken and Voragen at Wageningen University [Vincken et al (1994) Plant Physiol., 104, 99–107] and are able to degrade xyloglucans as described in Hayashi et al (1989) Plant. Physiol. Plant Mol. Biol., 40, 139–168. Vincken et al demonstrated the removal of xyloglucan coating from cellulase of the isolated apple cell wall by a xyloglucanase purified from Trichoderma viride (endo-IV-glucanase). This enzyme enhances the enzymatic degradation of cell wall-embedded cellulose and work in synergy with pectic enzymes. Rapidase LIQ+ from Gist-Brocades contains an xyloglucanase activity.

This xyloglucanase is incorporated into the cleaning compositions in accordance with the invention preferably at a level of from 0.0001% to 2%, more preferably from 0.0005% to 0.5%, most preferred from 0.001% to 0.1% pure enzyme by weight of the composition.

Preferred xyloglucanases for specific applications are alkaline xyloglucanases, ie enzymes having an enzymatic activity of at least 10%, preferably at least 25%, more preferably at least 40% of their maximum activity at a pH ranging from 7 to 12. More preferred xyloglucanases are enzymes having their maximum activity at a pH ranging from 7 to 12.

The above-mentioned enzymes may be of any suitable origin, such as vegetable, animal, bacterial, fungal and yeast origin. Origin can further be mesophilic or extremophilic (psychrophilic, psychrotrophic, thermophilic, barophilic, alkalophilic, acidophilic, halophilic, etc.). Purified or non-purified forms of these enzymes may be used. Nowadays, it is common practice to modify wild-type enzymes via protein/genetic engineering techniques in order to optimise their performance efficiency in the cleaning compositions of the invention. For example, the variants may be designed such that the compatibility of the enzyme to commonly encountered ingredients of such compositions is increased. Alternatively, the variant may be designed such that the optimal pH, bleach or chelant stability, catalytic activity and the like, of the enzyme variant is tailored to suit the particular cleaning application.

In particular, attention should be focused on amino acids sensitive to oxidation in the case of bleach stability and on surface charges for the surfactant compatibility. The isoelectric point of such enzymes may be modified by the substitution of some charged amino acids, e.g. an increase in isoelectric point may help to improve compatibility with anionic surfactants. The stability of the enzymes may be further enhanced by the creation of e.g. additional salt bridges and enforcing metal binding sites to increase chelant stability.

Use in the paper pulp industry

Further, it is contemplated that the mannanase of the present invention is useful in chlorine-free bleaching processes for paper pulp (chemical pulps, semichemical pulps, mechanical pulps or kraft pulps) in order to increase the brightness thereof, thus decreasing or eliminating the need for hydrogen peroxide in the bleaching process.

Use in the textile and cellulosic fiber processing industries

The mannanase of the present invention can be used in combination with other carbohydrate degrading enzymes (for instance xyloglucanase, xylanase, various pectinases) for preparation of fibers or for cleaning of fibers in combination with detergents.

In the present context, the term "cellulosic material" is intended to mean fibers, sewn and unsewn fabrics, including knits, wovens, denims, yarns, and toweling, made from cotton, cotton blends or natural or manmade cellulosics (e.g. originating from xylan-containing cellulose fibers such as from wood pulp) or blends thereof. Examples of blends are blends of cotton or rayon/viscose with one or more companion material such as wool, synthetic fibers (e.g. polyamide fibers, acrylic fibers, polyester fibers, polyvinyl alcohol fibers, polyvinyl chloride fibers, polyvinylidene chloride fibers, polyurethane fibers, polyurea fibers, aramid fibers), and cellulose-containing fibers (e.g. rayon/viscose, ramie, hemp, flax/linen, jute, cellulose acetate fibers, lyocell).

The processing of cellulosic material for the textile industry, as for example cotton fiber, into a material ready for garment manufacture involves several steps: spinning of the fiber into a yarn; construction of woven or knit fabric from the yarn and subsequent preparation, dyeing and finishing operations. Woven goods are constructed by weaving a filling yarn between a series of warp yarns; the yarns could be two different types.

Desizing: polymeric size like e.g. mannan, starch, CMC or PVA is added before weaving in order to increase the warp speed;

This material must be removed before further processing. The enzyme of the invention is useful for removal of mannan containing size.

Degradation of thickeners

Galactomannans such as guar gum and locust bean gum are widely used as thickening agents e.g. in food and print paste for textile printing such as prints on T-shirts. The enzyme or enzyme preparation according to the invention can be used for reducing the viscosity of eg residual food in processing equipment and thereby facilitate cleaning after processing. Further, it is contemplated that the enzyme or enzyme preparation is useful for reducing viscosity of print paste, thereby facilitating wash out of surplus print paste after textile printins.

Degradation or modification of plant material

The enzyme or enzyme preparation according to the invention is preferably used as an agent for degradation or modification of mannan, galactomannan, glucomannan or galactoglucomannan containing material originating from plants. Examples of such material is guar gum and locust bean gum.

The mannanase of the invention may be used in modifying the physical-chemical properties of plant derived material such as the viscosity. For instance, the mannanase may be used to reduce the viscosity of feed or food which contain mannan and to promote processing of viscous mannan containing material.

Coffee extraction

The enzyme or enzyme preparation of the invention may also be used for hydrolysing galactomannans present in a liquid coffee extract, preferably in order to inhibit gel formation during freeze drying of the (instant) coffee. Preferably, the mannanase of the invention is immobilized in order to reduce enzyme consumption and avoid contamination of the coffee. This use is further disclosed in EP-A-676 145.

Determination of catalytic activity (ManU) of mannanase Colorimetric Assay

Substrate: 0.2% AZCL-Galactomannan (Megazyme, Australia) from carob in 0.1M Glycin buffer, pH 10.0.

The assay is carried out in an Eppendorf Micro tube 1.5 ml on a thermomixer with stirring and temperature control of 40° C. Incubation of 0.750 ml substrate with 0.05 ml enzyme for 20 min, stop by centrifugation for 4 minutes at 15000 rpm. The colour of the supernatant is measured at 600 nm in a 1 cm cuvette.

One ManU (Mannanase units) gives 0.24 abs in 1 cm.

EXAMPLE 1

Production, Purification and Characterization of the *Bacillus subtilis* strain 168 mannanase The *Bacillus subtilisis* β-mannanase was produced and characterised as follows:

The *Bacillus subtilis* genome was searched for homology with a known Bacillus sp β-mannanase gene sequence (Mendoza et al., Biochemica et Biophysica Acta 1243:552–554, 1995). The coding region of ydhT, whose product was unknown, showed a 58% similarity to the known Bacillus β-Mannanase. The following oligonucleotides were designed to amplify the sequences coding for the mature portion of the putative β-mannanase: 5'-GCT CAA TTG GCG CAT ACT GTG TCG CCT GTG-3' and 5'-GAC GGA TCC CGG ATT CAC TCA ACG ATT GGC G-3'. Total genomic DNA from *Bacillus subtilis* strain 1A95 was used as a template to amplify the ydhT mature region using the aforementioned primers. PCR was performed using the GENE-AMP PCR Kit with AMPLITAQ DNA Polymerase (Perkin Elmer, Applied Biosystems, Foster City, Calif.). An initial melting period at 95° C. for 5 min was followed by 25 cycles of the following program: melting at 95° C. for 1 min, annealing at 55° C. for 2 min, and extension at 72° C. for 2 min. After the last cycle, the reaction was held at 72° C. for 10 min to complete extension. The PCR products were purified using QIAquick PCR purification kit (Qiagen, Chatsworth, Calif.).

The ydhT mature region amplified from *Bacillus subtilis* strain 1A95 was inserted into the expression vector pPG1524 (previously described) as follows. The amplified 1028 bp fragment was digested with Mfe I and BamH I. The expression vector pPG1527 was digested with EcoR I and BamH I. The restriction products were purified using QIAquick PCR purification kit (Qiagen, Chatsworth, Calif.). The two fragments were ligated using T4 DNA ligase (13 hr, 16° C.) and used to transform competent *E. coli* strain DH5-α. Ampicilin resistant colonies were cultured for DNA preparations. The DNA was then characterized by restriction analysis. Plasmid pPG3200 contains the mature region of the ydhT gene. Plasmid pPG3200 was then used to transform competent *Bacillus subtilis* strain PG 632 (Saunders et al., 1992).

Seven kanamycin resistant *Bacillus subtilis* clones and one PG 632 control clone were picked and grown in 20 ml of 20/20/5 media (20 g/l tryptone, 20 g/l yeast extract, 5 g/l NaCl) supplemented with 1 ml 25% maltrin, 120 µl 10 mM $MnCl_2$, and 201l of 50 mg/ml kanamycin. Clones were grown overnight in 250 ml baffled flasks shaking at 250 rpm at 37° C. for expression of the protein. Cells were spun out at 14,000 rpm for 15 minutes. One µl of each supernatant was diluted in 99 µl of 50 mM sodium acetate (pH 6.0). One µl of this dilution was assayed using the endo-1,4-β-mannanase Beta-Mannazyme Tabs (Megazyme, Ireland) according to the manufacturers instructions. Absorbance was read at 590 nm on a Beckman DU640 spectrophotometer. Clone 7 showed the highest absorbance of 1.67. The PG632 control showed no absorbance at 590 nm.

Supernatant was analyzed by SDS-PAGE on a 10–20% Tris-Glycine gel (Novex, San Diego, Calif.) to confirm expected protein size of 38 kDa. Samples were prepared as follows. A 500 µl sample of ydhT clone 7 and PG 632 supernatants were precipitated with 55.5 µl 100% Trichloroacetic acid (Sigma), washed with 100 µl 5% Trichloroacetic, resuspended in 50 µl of Tris-glycine SDS sample buffer(Novex) and boiled for five minutes. One µl of each sample was electrophoresed on the gel at 30 mA for 90 minutes. A large band of protein was observed to run at 38 kDa for ydhT clone 7.

A 10 l fermentation of Bacillus subtilis ydhT clone 7 was performed in a B.Braun Biostat C fermentator. Fermentation conditions were as follows. Cells were grown for 18h in a rich media similar to 20/20/5 at 37° C. At the end of the fermentation run, the cells were removed and the supernatant concentrated to 1 liter using a tangential flow filtration system. The final yield of β-mannanase in the concentrated supernatant was determined to be 3 g/l.

The purification of the β-mannanase from the fermentation supernatant was performed as follows: 500 ml of supernatant was centrifuged at 10,000 rpm for 10 min at 4° C. The centrifuged supernatant was then dialyzed overnight at 4° C. in two 4 l changes of 10 mM potassium phosphate (pH 7.2) through Spectrapor 12,000–14,000 mol.wt. cutoff membrane (Spectrum). The dialyzed supernatant was centrifuged at 10,000 rpm for 10 min at 4° C. A 200 ml Q Sepharose fast flow (Pharmacia) anion exchange column was equilibrated with 1 liter of 10 mM potassium phosphate (pH 7.2) at 20° C. and 300 ml of supernatant was loaded on column. Two flow through fractions of 210 ml (sample A) and 175 ml (sample B) were collected. The two fractions were assayed as before, except that the samples were diluted with 199 μl of 50 mM sodium acetate (pH 6.0), and they showed absorbance of 0.38 and 0.52 respectively. Two μl of each sample was added to 8 μl of Tris-glycine SDS sample buffer (Novex, Calif.) and boiled for 5 min. The resulting samples were electrophoresed on a 10–20% Tris-Glycine gel (Novex, Calif.) at 30 mA for 90 minutes. A major band corresponding to 38 kDa was present in each sample and comprised greater than 95% of the total protein. A BCA protein assay (Pierce) was performed on both samples according to the manufacturers instructions, using bovine serum albumin as standard. Samples A and B contained 1.3 mg/ml and 1.6 mg/ml of β-mannanase respectively. The identity of the protein was confirmed by ion spray mass spectrometry and amino terminal amino acid sequence analysis.

The purified P-Mannanase samples were used to characterize the enzyme activity as follows. All assays used endo-1,4-β-Mannanase Beta-Mannazyme Tabs (Megazyme, Ireland) as described above. Activity at pH range 3.0–9.0 were performed in 50 mM citrate phosphate buffer, for activity determination at pH 9.5, 50 mM CAPSO (Sigma), and for the pH range 10.0–11.0 50 mM CAPS buffer was used. The optimum pH for the *Bacillus subtilis* β-mannanase was found to be pH 6.0–6.5. Temperature activity profiles were performed in 50 mM citrate phosphate buffer (pH 6.5). The enzyme showed optimum activity at 40–45° C. The *Bacillus subtilis* β-mannanase retained significant activity at below 15° C. and above 80° C. Specific activity against β-1,4-Galactomannan was determined to be 160,000 μmol/min·mg β-mannanase using endo-1,4-β-mannanase Beta-Mannazyme Tabs (Megazyme, Ireland) according to the manufacturers directions.

The nucleotide sequence encoding the mature region of a *Bacillus subtilis* β-mannanase according to the invention is shown in SEQ ID NO:1, and the derived amino acid sequence is shown in SEQ ID NO:2.

EXAMPLE 2

Use of the enzyme of the invention in detergents

The purified enzyme obtained as described in example 1 showed improved cleaning performance when tested at a level of 1 ppm in a miniwash test using a conventional commercial liquid detergent. The test was carried out under conventional North American wash conditions.

LITERATURE

Lever, M. (1972) A new reaction for colormetric determination of carbohydrates. Anal. Biochem. 47, 273–279.

N. C. Carpita and D. M. Gibeaut (1993) The Plant Journal 3:1–30.

Diderichsen, B., Wedsted, U., Hedegaard, L., Jensen, B. R., Sjøholm, C. (1990) Cloning of aldB, which encodes alpha-acetolactate decarboxylase, an exoenzyme from *Bacillus brevis*. J. Bacteriol. 172:4315–4321.

We claim:

1. An isolated mannanase which is
   (a) a polypeptide comprising an amino acid sequence of SEQ ID NO:2, or
   (b) a polypeptide which has an amino acid sequence which has at least 90% identity with the amino acid sequence of SEQ ID NO:2, or
   (c) a fragment of SEQ ID NO:2 that has mannanase activity.

2. The mannanase of claim 1 which comprises the amino acid sequence of SEQ ID NO:2.

3. The mannanase of claim 1 which has an amino acid sequence which has at least 95% identity with the amino acid sequence of SEQ ID NO:2.

4. The mannanase of claim 3 which has an amino acid sequence which has at least 98% identity with the amino acid sequence of SEQ ID NO:2.

5. The mannanase of claim 3 which is obtained from *Bacillus subtilis*.

6. The mannanase of claim 4 which is obtained from *Bacillus subtilis*.

7. An enzyme preparation comprising a mannanase of claim 1 and one or more enzymes selected from the group consisting of proteases, cellulases (endoglucanases), β-glucanases, hemicellulases, lipases, peroxidases, laccases, α-amylases, glucoamylases, cutinases, pectinases, reductases, oxidases, phenoloxidases, ligninases, pullulanases, pectate lyases, xyloglacanases, xylanases, pectin acetyl esterases, polygalacturonases, rhamnogalacturonases, pectin lyases, other mannanases, pectin methylesterases, cellobiohydrolases, transglutaminases; and mixtures thereof.

8. A cleaning composition comprising a mannanase of claim 1 and a surfactant.

9. The cleaning composition of claim 8, further comprising one or more enzymes selected from the group consisting of proteases, cellulases (endoglucanases), β-glucanases, hemicellulases, lipases, peroxidases, laccases, α-amylases, glucoamylases, cutinases, pectinases, reductases, oxidases, phenoloxidases, ligninases, pullulanases, pectate lyases, xyloglucanases, xylanases, pectin acetyl esterases, polygalacturonases, rhamnogalacturonases, pectin lyases, other mannanases, pectin methylesterases, cellobiohydrolases, transglutaminases; and mixtures thereof.

10. The cleaning composition of claim 8, further comprising an enzyme selected from the group consisting of cellulases, amylases, pectin degrading enzymes and/or xyloglucanases; and another detergent ingredient.

11. The cleaning composition of claim 8, wherein the mannanase is present at a level of from 0.0001% to 2% pure enzyme by weight of total composition.

12. The cleaning composition of claim 10, wherein the enzyme is present at a level of from 0.0001% to 2% pure enzyme by weight of total composition.

13. The cleaning composition of claim 10, wherein the enzyme is an amylase.

14. The cleaning composition of claim 13, further comprising an enzyme selected from the group consisting of cellulase, pectin degrading enzyme, xyloglucanase and mixtures thereof.

15. The cleaning composition of claim 10, wherein the enzyme is alkaline.

16. The cleaning composition of claim 8, wherein the surfactant is selected from teh group consisting of anionic, nonionic, cationic surfactant, and mixtures thereof.

17. The cleaning composition of claim 8, furthing comprising a bleaching agent.

18. The cleaning composition of claim 8, further comprising a builder.

19. The composition of claim 8, wherein the surfactant is a cationic surfactant comprising two long chain lengths.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1011 base pairs
      (B) TYPE: nucleic acid
      (C) STRANDEDNESS: single
      (D) TOPOLOGY: linear (xi) SEQUENCE DESCRIPTION: SEQ ID NO:1:

```
CATACTGTGT CGCCTGTGAA TCCTAATGCC CAGCAGACAA CAAAAACAGT GATGAACTGG      60

CTTGCGCACC TGCCGAACCG AACGGAAAAC AGAGTCCTTT CCGGAGCGTT CGGAGGTTAC     120

AGCCATGACA CATTTTCTAT GGCTGAGGCT GATAGAATCC GAAGCGCCAC CGGGCAATCG     180

CCTGCTATTT ATGGCTGCGA TTATGCCAGA GGATGGCTTG AAACAGCAAA TATTGAAGAT     240

TCAATAGATG TAAGCTGCAA CGGCGATTTA ATGTCGTATT GGAAAAATGG CGGAATTCCG     300

CAAATCAGTT TGCACCTGGC GAACCCTGCT TTTCAGTCAG GGCATTTTAA AACACCGATT     360

ACAAATGATC AGTATAAAAA CATATTAGAT TCAGCAACAG CGGAAGGGAA GCGGCTAAAT     420

GCCATGCTCA GCAAAATTGC TGACGGACTT CAAGAGTTGG AGAACCAAGG TGTGCCTGTT     480

CTGTTCAGGC CGCTGCATGA AATGAACGGC GAATGGTTTT GGTGGGGACT CACATCATAT     540

AACCAAAAGG ATAATGAAAG AATCTCTCTA TATAAACAGC TCTACAAGAA AATCTATCAT     600

TATATGACCG ACACAAGAGG ACTTGATCAT TTGATTTGGG TTTACTCTCC CGACGCCAAC     660

CGAGATTTTA AAACTGATTT TTACCCGGGC GCGTCTTACG TGGATATTGT CGGATTAGAT     720

GCGTATTTTC AAGATGCCTA CTCGATCAAT GGATACGATC AGCTAACAGC GCTTAATAAA     780
```

```
CCATTTGCTT TTACAGAAGT CGGCCCGCAA ACAGCAAACG GCAGCTTCGA TTACAGCCTG    840

TTCATCAATG CAATAAAACA AAAATATCCT AAAACCATTT ACTTTCTGGC ATGGAATGAT    900

GAATGGAGCG CAGCAGTAAA CAAGGGTGCT TCAGCTTTAT ATCATGACAG CTGGACACTC    960

AACAAGGGAG AAATATGGAA TGGTGATTCT TTAACGCCAA TCGTTGAGTG A            1011
```

(2) INFORMATION FOR SEQ ID NO:2:

(i) SEQUENCE CHARACTERISTICS:
        (A) LENGTH: 336 amino acids
        (B) TYPE: amino acid
        (C) STRANDEDNESS: single
        (D) TOPOLOGY: linear (xi) SEQUENCE DESCRIPTION: SEQ ID NO:2:

```
His Thr Val Ser Pro Val Asn Pro Asn Ala Gln Gln Thr Thr Lys Thr
 1               5                  10                  15

Val Met Asn Trp Leu Ala His Leu Pro Asn Arg Thr Glu Asn Arg Val
             20                  25                  30

Leu Ser Gly Ala Phe Gly Gly Tyr Ser His Asp Thr Phe Ser Met Ala
         35                  40                  45

Glu Ala Asp Arg Ile Arg Ser Ala Thr Gly Gln Ser Pro Ala Ile Tyr
     50                  55                  60

Gly Cys Asp Tyr Ala Arg Gly Trp Leu Glu Thr Ala Asn Ile Glu Asp
 65                  70                  75                  80

Ser Ile Asp Val Ser Cys Asn Gly Asp Leu Met Ser Tyr Trp Lys Asn
                 85                  90                  95

Gly Gly Ile Pro Gln Ile Ser Leu His Leu Ala Asn Pro Ala Phe Gln
            100                 105                 110

Ser Gly His Phe Lys Thr Pro Ile Thr Asn Asp Gln Tyr Lys Asn Ile
        115                 120                 125

Leu Asp Ser Ala Thr Ala Glu Gly Lys Arg Leu Asn Ala Met Leu Ser
    130                 135                 140

Lys Ile Ala Asp Gly Leu Gln Glu Leu Glu Asn Gln Gly Val Pro Val
145                 150                 155                 160

Leu Phe Arg Pro Leu His Glu Met Asn Gly Glu Trp Phe Trp Trp Gly
                165                 170                 175

Leu Thr Ser Tyr Asn Gln Lys Asp Asn Glu Arg Ile Ser Leu Tyr Lys
            180                 185                 190

Gln Leu Tyr Lys Lys Ile Tyr His Tyr Met Thr Asp Thr Arg Gly Leu
        195                 200                 205

Asp His Leu Ile Trp Val Tyr Ser Pro Asp Ala Asn Arg Asp Phe Lys
    210                 215                 220

Thr Asp Phe Tyr Pro Gly Ala Ser Tyr Val Asp Ile Val Gly Leu Asp
225                 230                 235                 240

Ala Tyr Phe Gln Asp Ala Tyr Ser Ile Asn Gly Tyr Asp Gln Leu Thr
                245                 250                 255

Ala Leu Asn Lys Pro Phe Ala Phe Thr Glu Val Gly Pro Gln Thr Ala
            260                 265                 270

Asn Gly Ser Phe Asp Tyr Ser Leu Phe Ile Asn Ala Ile Lys Gln Lys
        275                 280                 285

Tyr Pro Lys Thr Ile Tyr Phe Leu Ala Trp Asn Asp Glu Trp Ser Ala
    290                 295                 300

Ala Val Asn Lys Gly Ala Ser Ala Leu Tyr His Asp Ser Trp Thr Leu
305                 310                 315                 320
```

```
-continued

Asn Lys Gly Glu Ile Trp Asn Gly Asp Ser Leu Thr Pro Ile Val Glu
            325                 330                 335

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:3:

GCTCAATTGG CGCATACTGT GTCGCCTGTG                                      30

(2) INFORMATION FOR SEQ ID NO:4:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

GACGGATCCC GGATTCACTC AACGATTGGC G                                    31
```